(12) United States Patent
Baikerikar et al.

(10) Patent No.: US 7,943,725 B2
(45) Date of Patent: May 17, 2011

(54) 1,3/1,4-CYCLOHEXANE DIMETHANOL BASED MONOMERS AND POLYMERS

(75) Inventors: Kiran K. Baikerikar, Midland, MI (US); Michael L. Tulchinsky, Midland, MI (US); John N. Argyropoulos, Midland, MI (US)

(73) Assignee: Dow Global Technologies LLC

( * ) Notice: Subject to any disclaimer, the term of this patent is extended or adjusted under 35 U.S.C. 154(b) by 269 days.

(21) Appl. No.: 12/160,001

(22) PCT Filed: Dec. 7, 2006

(86) PCT No.: PCT/US2006/046696
§ 371 (c)(1),
(2), (4) Date: Oct. 20, 2008

(87) PCT Pub. No.: WO2007/092071
PCT Pub. Date: Aug. 16, 2007

(65) Prior Publication Data
US 2009/0198014 A1    Aug. 6, 2009

Related U.S. Application Data

(60) Provisional application No. 60/765,430, filed on Feb. 3, 2006.

(51) Int. Cl.
*C08G 63/00* (2006.01)
*C07C 31/13* (2006.01)

(52) U.S. Cl. ........ 528/307; 568/822; 568/670; 524/849; 524/553; 524/554; 524/457; 528/302

(58) Field of Classification Search .................. 524/849, 524/553, 554, 457; 568/822, 670; 560/220; 528/302, 307
See application file for complete search history.

(56) References Cited

U.S. PATENT DOCUMENTS

| | | | | |
|---|---|---|---|---|
| 2,917,549 A * | 12/1959 | Knowles et al. | ............. | 568/831 |
| 2,956,961 A * | 10/1960 | Kibler et al. | ................. | 442/226 |
| 4,177,315 A | 12/1979 | Ubersax | | |
| 4,348,462 A | 9/1982 | Chung | | |
| 4,554,343 A | 11/1985 | Jackson et al. | | |
| 4,578,453 A * | 3/1986 | Jackson et al. | ................ | 528/302 |
| 4,600,768 A | 7/1986 | Jackson, Jr. et al. | | |
| 4,775,732 A | 10/1988 | Lapin | | |
| 5,017,679 A | 5/1991 | Chang et al. | | |
| 5,387,752 A * | 2/1995 | Scarlett et al. | ................ | 568/831 |
| 5,502,121 A * | 3/1996 | Scott et al. | .................... | 525/444 |
| 5,523,382 A | 6/1996 | Beavers et al. | | |
| 5,541,268 A * | 7/1996 | Fenn et al. | ................... | 428/431 |
| 5,552,512 A * | 9/1996 | Sublett | .......................... | 528/308 |
| 5,773,554 A | 6/1998 | Dickerson et al. | | |
| 6,252,121 B1 | 6/2001 | Argyropoulos et al. | | |
| 6,255,523 B1 | 7/2001 | Panandiker et al. | | |
| 6,541,595 B2 * | 4/2003 | Panandiker et al. | ............ | 528/45 |
| 6,706,779 B2 | 3/2004 | Bahadur et al. | | |
| 7,244,792 B2 | 7/2007 | Agarwal et al. | | |
| 7,375,144 B2 * | 5/2008 | Gilmer | ............................ | 522/92 |
| 7,687,594 B2 | 3/2010 | Hung et al. | | |
| 2004/0132924 A1 | 7/2004 | Weiss et al. | | |
| 2004/0151838 A1 * | 8/2004 | Fenn et al. | ..................... | 427/384 |
| 2005/0245711 A1 | 11/2005 | Narayan-Sarathy et al. | | |
| 2008/0152926 A1 | 6/2008 | Baikerikar et al. | ......... | 428/422.8 |
| 2009/0142981 A1 * | 6/2009 | Arendt et al. | .................. | 442/263 |
| 2009/0178306 A1 * | 7/2009 | Vairo et al. | ..................... | 36/25 R |
| 2009/0192286 A1 * | 7/2009 | Argyropoulos et al. | ...... | 528/307 |
| 2009/0253585 A1 * | 10/2009 | Diatchenko et al. | ............. | 506/9 |
| 2009/0253858 A1 | 10/2009 | Argyropoulos et al. | | |
| 2011/0039982 A1 * | 2/2011 | Hefner et al. | ................. | 523/400 |

FOREIGN PATENT DOCUMENTS

| CA | 2548040 | 6/2005 |
|---|---|---|
| WO | 9013587 | 11/1990 |

OTHER PUBLICATIONS

John Argyropoulos, et al., "Unoxol TM Diol: A New Liquid Cycloaliphatic Diol for Coatings Applications", Paint & Coatings Industry magazine, Jun. 2006, p. 1-5.
Takeuchi Hiroshi, et al., "Novel Di(meth)acrylate and Production Thereof", Machine Translation, JP 07-304708.
Eiichi Okazaki, et al., "Manufacture of liquid polymeriable (meth)acrylates for preparation of coatings.", Machine Translation, JP 3374471 B2.
W.F.H. Borman, "Molecular Weight-Viscosity Relationships for Poly(1,4-butylene Terephthalate)", Journal of Applied Polymer Science, vol. 22, 2119-2126, 1978.

* cited by examiner

*Primary Examiner* — Mark Eashoo
*Assistant Examiner* — Jane L Stanley

(57) ABSTRACT

A mixture of compounds useful to make a polymer or a prepolymer, the mixture of compounds including compounds having the formula I; wherein $R_1$ is H, acryloyl, methacryloyl or vinyl, wherein $R_2$ is acryloyl, methacryloyl or vinyl, wherein compounds having the formula I consist of a mixture of cis and trans-1,3- and 1,4-substituted cyclohexane and wherein the trans-1,4-substituted cyclohexane content of the compounds having the formula I is less than forty mole percent. A process for producing a mixture of compounds including compounds having the formula II: wherein compounds having the formula II consist of a mixture of cis and trans-1,3- and 1,4-methanol substituted cyclohexane and wherein the trans-1,4-methanol substituted cyclohexane content of the compounds having the formula II is less than twenty five mole percent.

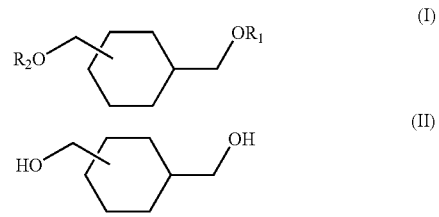

10 Claims, No Drawings

1,3/1,4-CYCLOHEXANE DIMETHANOL BASED MONOMERS AND POLYMERS

CROSS REFERENCE TO RELATED APPLICATIONS

This application is a 371 of PCT/US06/046696 filed Dec. 7, 2006, which claims the benefit of U.S. Provisional Application Ser. No. 60/765,430, filed Feb. 3, 2006.

BACKGROUND OF THE INVENTION

The instant invention is in the field of monomers and polymers based on a mixture of cis and trans 1,3- and 1,4-cyclohexane dimethanol and methods to produce such mixtures.

Radiation cured (typically free radical UV light photopolymerization) coatings and inks are widely used in the coatings and printing industry. Radiation cured coating and ink formulations based on prior art cyclohexane dimethanol diacrylates provide excellent end-use properties for the cured coating (such as hardness and strength) but such formulations are difficult to use because the cyclohexane dimethanol diacrylates are solid materials at room temperature and often are insoluble in most acrylates. Liquid coating and ink formulations based on ethoxylated or propoxylated cyclohexane dimethanol diacrylates are known but the resulting coating has poorer end use properties. It would be an advance in the art of coating and ink formulations based on cyclohexane dimethanol chemistry if such formulations were discovered that were both liquid at room temperature and provided improved end use properties for the resulting coating.

SUMMARY OF THE INVENTION

The instant invention solves the above-stated problem. The instant invention provides a mixture of cyclohexane dimethanol based acrylates and methacrylates which are liquid at room temperature and which can be used to obtain coatings having excellent hardness, strength, clarity, abrasion resistance, adhesion, stain resistance and solvent resistance properties.

In one embodiment, the instant invention is a mixture of compounds useful to make a polymer or a prepolymer, the mixture of compounds comprising compounds having the formula I:

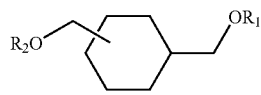

I wherein $R_1$ is H, acryloyl, methacryloyl or vinyl, wherein $R_2$ is acryloyl, methacryloyl or vinyl, wherein compounds having the formula I consist of a mixture of cis and trans-1,3- and 1,4-substituted cyclohexane and wherein the trans-1,4-substituted cyclohexane content of the compounds having the formula I is less than forty mole percent.

In another embodiment, the instant invention is a process for producing a mixture of compounds comprising compounds having the formula II:

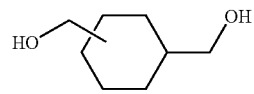

II wherein compounds having the formula II consist of a mixture of cis and trans-1,3- and 1,4-methanol substituted cyclohexane and wherein the trans-1,4-methanol substituted cyclohexane content of the compounds having the formula II is less than twenty five mole percent, characterized by the step of: distilling a mixture of cis and trans-1,3- and 1,4-methanol substituted cyclohexane wherein the trans-1,4-methanol substituted cyclohexane content of the compounds is greater than twenty five mole percent to produce a distilled fraction and a residue fraction, the residue fraction being the mixture of cis and trans-1,3- and 1,4-methanol substituted cyclohexane wherein the trans-1,4-methanol substituted cyclohexane content of the compounds having the formula II is less than twenty five mole percent.

In yet another embodiment, the instant invention is a prepolymer comprising units having the formula III:

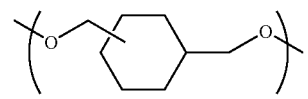

III wherein the units having the formula III consist of a mixture of cis and trans-1,3- and 1,4-substituted cyclohexane and wherein the trans-1,4-substituted cyclohexane content of the units havivg the formula III is less than forty mole percent and wherein the prepolymer is selected from the group consisting of polyester acrylates, polyester methacrylates, polycarbonate acrylates, polycarbonate methacrylates, polyurethane acrylates and polyurethane methacrylates.

DETAILED DESCRIPTION

In one embodiment, the instant invention is a mixture of compounds useful to make a polymer or a prepolymer, the mixture of compounds comprising compounds having the formula I:

I wherein $R_1$ is H, acryloyl, methacryloyl or vinyl, wherein $R_2$ is acryloyl, methacryloyl or vinyl, wherein compounds having the formula I consist of a mixture of cis and trans-1,3- and 1,4-substituted cyclohexane and wherein the trans-1,4-substituted cyclohexane content of the compounds having the formula I is less than forty mole percent. Preferably, the trans-1,4-substituted cyclohexane content of the compounds having the formula I is less than twenty five mole percent. More preferably, the trans-1,4-substituted cyclohexane content of the compounds having the formula I is less than fifteen mole percent. Preferably, the mixture of compounds comprising compounds having the formula I is a liquid at room temperature. The mixture of compounds comprising compounds having the formula I can be used, for example and without limitation, in coating, ink, adhesive and elastomer applications. A prepolymer is defined with regard to this embodiment as a derivative of the compounds having the formula I which derivative is then used to make a polymer.

The mixture of compounds having the formula I can be made by: (a) acrylating (or methacrylating) UNOXOL brand diol (a mixture of cis and trans-1,3- and 1,4-cyclohexane dimethanol available from The Dow Chemical Company) to produce a product that is a mixture of a liquid and a solid at room temperature; and (b) separating the liquid product from the solid product (the liquid product being the desired product). Alternatively, the mixture of compounds having the formula I can be made by: (a) distilling UNOXOL brand diol (a mixture of cis and trans-1,3- and 1,4-cyclohexane dimethanol available from The Dow Chemical Company) to produce a distilled fraction and a residue fraction; and (b) acrylating (or methacrylating) the residue fraction. The mixture of cis and trans-1,3- and 1,4-cyclohexane dimethanol for either of these two processes can be made according to the teachings of U.S. Pat. No. 6,252,121. The vinyl derivatives having the formula I can be made by reacting the mixture of cis and trans-1,3- and 1,4-cyclohexane dimethanol with acetylene at a pressure of 3-20 bar at 120-180° C. using a potassium hydroxide catalyst.

The instant invention is also a process for producing a mixture of compounds comprising compounds having the formula II:

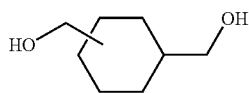

II wherein compounds having the formula II consist of a mixture of cis and trans-1,3- and 1,4-methanol substituted cyclohexane and wherein the trans-1,4-methanol substituted cyclohexane content of the compounds having the formula II is less than twenty five mole percent, characterized by the step of: distilling a mixture of cis and trans-1,3- and 1,4-methanol substituted cyclohexane wherein the trans-1,4-methanol substituted cyclohexane content of the compounds is greater than twenty five mole percent to produce a distilled fraction and a residue fraction, the residue fraction being the mixture of cis and trans-1,3- and 1,4-methanol substituted cyclohexane wherein the trans-1,4-methanol substituted cyclohexane content of the compounds having the formula II is less than twenty five mole percent. Preferably, the trans-1,4-methanol substituted cyclohexane content of the compounds having the formula II is less than fifteen mole percent. Compounds having the formula II can be used as a precursor in the preparation of compounds having the formula I.

The compounds having the formula II can be ethoxylated or propoxylated to prepare the mixture of compounds having the formula IV:

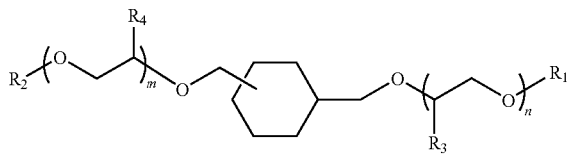

IV wherein $R_1$ is H, acryloyl, methacryloyl or vinyl, wherein $R_2$ is acryloyl, methacryloyl or vinyl, wherein n is an integer in the range of from one to ten, wherein m is an integer in the range of from one to ten, wherein $R_3$ is H or methyl, wherein $R_4$ is H or methyl.

The compounds having the formula II can be reacted with dicarboxylic acids and then acrylated or methacrylated to produce polyester acrylate prepolymers or polyester methacrylate prepolymers. The compounds having the formula II can be reacted with dicarbonates and then acrylated or methacrylated to produce polycarbonate acrylate prepolymers or polycarbonate methacrylate prepolymers. And, the compounds having the formula II can be reacted with diisocyanates and then acrylated or methacrylated to produce polyurethane acrylate prepolymers or polyurethane methacrylate prepolymers. A common feature of all such prepolymers is a unit having the formula III:

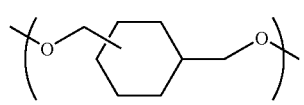

III wherein the units having the formula III consist of a mixture of cis and trans-1,3- and 1,4-substituted cyclohexane and wherein the trans-1,4-substituted cyclohexane content of the units having the formula III is less than forty mole percent (preferably less than twenty five mole percent and more preferably less than fifteen mole percent).

The acrylate, methacrylate, and vinyl monomers and prepolymers of the instant invention are typically polymerized by free radical polymerization techniques such as by the use of a peroxide polymerization catalyst. However, such monomers and prepolymers of the instant intention are most preferably polymerized by free radical photopolymerization techniques using a photoinitiator activated by UV light. For applications in which the formulation is; cured by electron beam (EB) radiation, a photoinitiator is not required to initiate polymerization.

The monomers and prepolymers of the instant invention can be blended with a filler, preferably inorganic nanoparticles such as colloidal silica to prepare colloidal silica preparations (such as a colloidal silica acrylate system). Colloidal silica acrylates provide, for example and without limitation, enhanced scratch resistance to acrylate coatings. Colloidal silica acrylates are disclosed in, for example and without limitation, U.S. Pat. Nos. 4,177,315 and 4,348,462.

EXAMPLES

The following examples and comparative examples show that the mixture of compounds of the instant invention can be used to obtain coatings having excellent hardness, strength, clarity, abrasion resistance, adhesion, stain resistance and solvent resistance properties. All parts and percentages are by weight unless otherwise indicated.

Example 1

2.5 kilograms of UNOXOL brand diol (a mixture of cis and trans-1,3- and 1,4-cyclohexane dimethanol available from The Dow Chemical Company having a trans-1,4-diol content of about 30% by weight) is fractionally distilled at 123-134° C. and 0.7 mm Hg using a 50 cm Oldershaw column (15 trays). The residue fraction is analyzed by gas chromatography and found to contain about 15% by weight of the trans-1,4-isomer. 0.1 kilogram of the residue is mixed with 400 milliliters of toluene and 252 grams of diisopropylethylamine and cooled in an ice bath. 153 grams of acryloyl chloride is added and mixed for two hours. Then the mixture is warmed to room temperature and washed with water (2×300 ml), 0.1 M citric acid (5×300 ml), saturated NaHCO₃ (300 ml), saturated NaCl (300 ml) and dried over MgSO₄. The toluene is removed in vacuum, and the residue is dried at 60° C. and 0.7 mm Hg to give a crude liquid product. The crude liquid product is chromatographed on silica gel using hexane-ethyl acetate (a gradient elution from 40:1 to 10:1). The fractions from the silica gel column are combined, polymerization inhibitor MEHQ (100 ppm) is added, the solvent is evaporated, and the residue is dried in vacuum to produce a purified liquid product. The purified liquid product is characterized by NMR and gas chromatography as a mixture of compounds comprising compounds having the formula I:

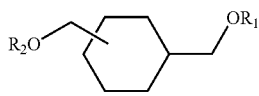

wherein $R_1$ is acryloyl, wherein $R_2$ is acryloyl, wherein compounds having the formula I consist of a mixture of cis and trans 1,3 and 1,4 substituted cyclohexane and wherein the trans 1,4 substituted cyclohexane content of the compounds having the formula I is about 13.6% by weight.

Five parts per hundred of 1-hydroxycyclohexylphenyl ketone (IRGACURE 184 brand photoinitiator from Ciba) is mixed with the purified liquid product and coated on a glass test substrate and cured by exposure to UV radiation to produce a 10 micrometer thick coating (plus or minus 2 micrometers) having a universal hardness of 193 N/mm²; a Vickers hardness of 18.6 (determined by Fischerscope H100C dynamic microindentation); a modulus of 4.84 GPa; a light transmittance of 91 percent; an initial haze of 0.15% according to ASTM test D1003/D1044; a pencil hardness of 3H according to ASTM test D3363; and a MEK rub test of greater than 100 rubs according to ASTM test D5402.

Five parts per hundred of 1-hydroxy cyclohexyl phenyl ketone (IRGACURE 184 brand photoinitiator from Ciba) is mixed with the purified liquid product and coated on a polycarbonate substrate and cured by exposure to UV radiation to produce a 35 micrometer thick coating (plus or minus 2 micrometers) having a universal hardness of 180 N/mm²; an initial haze of 0.61% according to ASTM test D1003/D1044; a pencil hardness of HB according to ASTM test D3363; an MEK rub test of greater than 200 rubs according to ASTM test D5402, an adhesion of 5B according to ASTM test D3359, an abrasion resistance of 18.9% change in haze after 100 Taber cycles with CS-10 F wheels and a 1000 gram load according to ASTM test D1044 and a chemical and stain resistance score according to ASTM test D1308 (wherein a score of 0 indicates no stain and a score of 5 indicates a maximum stain) of 0, 1, 0, 0, 0, 0, 0 and 0 respectively for tap water, ethanol, vinegar, black dye, dilute caustic soda, yellow mustard, Betadine and ammonia water.

Example 2

Five parts per hundred of 1-hydroxycyclohexylphenyl ketone (IRGACURE 184 brand photoinitiator from Ciba) is mixed with a 50:50 blend by weight of the purified liquid product of Example 1 and an aliphatic urethane diacrylate oligomer (EBECRYL 8402 from Cytec) and coated on a polycarbonate substrate and cured by exposure to UV radiation to produce a 35 micrometer thick coating (plus or minus 2 micrometers) having a universal hardness of 151 N/mm²; an initial haze of 0.63% according to ASTM test D1003/D1044; a pencil hardness; of B according to ASTM test D3363; an MEK rub test of greater than 100 rubs according to ASTM test D5402, an adhesion of 5B according to ASTM test D3359, an abrasion resistance of 14.1% change in haze after 100 Taber cycles with CS-10 F wheels and a 1000 gram load according to ASTM test D1044.

Example 3

0.1 kilogram of UNOXOL brand diol (a mixture of cis and trans-1,3- and 1,4-cyclohexane dimethanol available from The Dow Chemical Company having a trans-1,4-diol content of about 30% by weight) is mixed with 400 milliliters of toluene and 252 grams of diisopropylethylamine and cooled in an ice bath. 153 grams of acryloyl chloride is added and mixed for two hours. Then the mixture is warmed to room temperature and filtered to remove the solid phase. The filtrate is washed with water (2×300 ml), 0.1 M citric acid (5×300 ml), saturated NaHCO₃ (300 ml), saturated NaCl (300 ml) and dried over MgSO₄. The toluene is removed in vacuum, and the residue is dried at 60° C. and 0.7 mm Hg to give about 180 g of crude liquid product. The crude liquid product is chromatographed on silica gel using hexane-ethyl acetate (a gradient elution from 40:1 to 10:1). The fractions from the silica gel column are combined, polymerization inhibitor MEHQ (100 ppm) is added, the solvent is evaporated, and the residue is dried in vacuum to produce 138 grams of purified product consisting of a liquid phase and a solid phase which are separated by filtration. The purified liquid product is characterized by NMR and gas chromatography to be a mixture of compounds comprising compounds having the formula I:

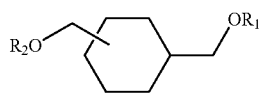

wherein $R_1$ and $R_2$ are acryloyl, wherein compounds having the formula I consist of a mixture of cis and trans-1,3- and 1,4-substituted cyclohexane and wherein the trans-1,4-substituted cyclohexane content of the compounds having the formula I is about 6.1% by weight.

The solid phase is characterized by NMR and gas chromatography to be mixture of compounds comprising compounds having the formula I:

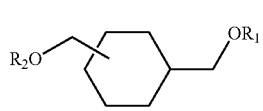

wherein $R_1$ and $R_2$ are acryloyl, wherein compounds having the formula I consist of a mixture of cis and trans-1,3- and 1,4-substituted cyclohexane and wherein the trans-1,4-substituted cyclohexane content of the compounds having the formula I is about 52% by weight.

Five parts per hundred of 1-hydroxycyclohexylphenyl ketone (IRGACURE 184 brand photoinitiator from Ciba) is mixed with the purified liquid product and coated on a glass test substrate and cured by exposure to UV radiation to produce a 10 micrometer thick coating plus or minus 2 micrometers) having a universal hardness of 198 N/mm$^2$; a Vickers hardness of 19; a modulus of 4.94 GPa; a light transmittance of 91 percent; an initial haze of 0.08% according to ASTM test D1003/D1044; a pencil hardness of 3H according to ASTM test D3363; and a MEK rub test of greater than 100 rubs according to ASTM test D5402.

Comparative Example 1

Five parts per hundred of 1-hydroxycyclohexylphenyl ketone (IRGACURE 184 brand photoinitiator from Ciba) is mixed with Sartomer SR 238 brand monomer (hexanediol diacrylate) and coated on a glass test substrate and cured by exposure to UV radiation to produce a 10 micrometer thick coating (plus or minus 2 micrometers) having a universal hardness of 114 N/mm$^2$; a Vickers hardness of 10.5; a modulus of 2.78 GPa; a light transmittance of 90.8 percent; an initial haze of 0.07% according to ASTM test D1003/D1044; a pencil hardness of H according to ASTM test D3363; a MEK rub test of greater than 100 rubs according to ASTM test D5402 and a stain resistance score (for 35 micrometer coatings on a polycarbonate substrate) according to ASTM test D1308 of 0, 0, 0, 2, 0, 1, 0 and 1 respectively for tap water, ethanol, vinegar, black dye, dilute caustic soda, yellow mustard, Betadine and ammonia water.

When coated on a polycarbonate test substrate and cured by exposure to UV radiation to produce a 35 micrometer thick coating (plus or minus 2 micrometers), the coating has a universal hardness of 104 N/mm$^2$; an initial haze of 0.67% according to ASTM test D1003/D1044; a pencil hardness of HB according to ASTM test D3363; a MEK rub test of greater than 200 rubs according to ASTM test D5402; an adhesion of 5B according to ASTM test D3359, an abrasion resistance of 20.0% after 100 Taber cycles with CS-10 F wheels and a 1000 gram load according to ASTM test D1044.

Comparative Example 2

Five parts per hundred of 1-hydroxycyclohexylphenyl ketone (IRGACURE 184 brand photoinitiator from Ciba) is mixed with Sartomer SR 306 brand monomer (tripropylene glycol diacrylate) and coated on a glass test substrate and cured by exposure to UV radiation to produce a 10 micrometer thick coating (plus or minus 2 micrometers) having a universal hardness of 116 N/mm 2; a Vickers hardness of 8.78; a modulus of 3.07 GPa; a light transmittance of 91.1 percent; an initial haze of 0.06% according to ASTM test D1003/D1044; a pencil hardness of B according to ASTM test D3363; an MEK rub test of greater than 100 rubs according to ASTM test D5402 and a stain resistance score (for 35 micrometer coatings on a polycarbonate substrate) according to ASTM test D1308 of 1, 2, 1, 3, 2, 1, 0 and 1 respectively for tap water, ethanol, vinegar, black dye, dilute caustic soda, yellow mustard, Betadine and ammonia water.

When coated on a polycarbonate test substrate and cured by exposure to UV radiation to produce a 35 micrometer thick coating (plus or minus 2 micrometers), the coating has a universal hardness of 105 N/mm$^2$; an initial haze of 0.68% according to ASTM test D1003/D1044; a pencil hardness of 2B according to ASTM test D3363; a MEK rub test of greater than 200 rubs according to ASTM test D5402; an adhesion of 1B according to ASTM test D3359, an abrasion resistance of 36.8% after 100 Taber cycles with CS-10 F wheel and a 1000 gram load according to ASTM test D1044.

Comparative Example 3

Five parts per hundred of 1-hydroxycyclohexylphenyl ketone (IRGACURE 184 brand photoinitiator from Ciba) is mixed with Sartomer SR 508 brand monomer (dipropylene gtycoldiacrylate) and coated on a glass test substrate and cured by exposure to UV radiation to produce a 10 micrometer thick coating (plus or minus 2 micrometers) having a universal hardness of 156 N/mm$^2$; a Vickers hardness of 12.4; a modulus of 4.34 GPa; a light transmittance of 91.0 percent; an initial haze of 0.05% according to ASTM test D1003/D1044; a pencil hardness of H according to ASTM test D3363; an MEK rub test of greater than 100 rubs according to ASTM test D5402 and a stain resistance score (for 35 micrometer coatings on a polycarbonate substrate) according to ASTM test D1308 of 0, 1, 0, 2, 1, 1, 0 and 1 respectively for tap water, ethanol, vinegar, black dye, dilute caustic soda, yellow mustard, Betadine and ammonia water.

When coated on a polycarbonate test substrate and cured by exposure to UV radiation to produce a 35 micrometer thick coating (plus or minus 2 micrometers), the coating has a universal hardness of 142 N/mm$^2$; an initial haze of 0.62% according to ASTM test D1003/D1044; a pencil hardness of 2B according to ASTM test D3363; a MEK rub test of greater than 200 rubs according to ASTM test D5402; an adhesion of 0B according to ASTM test D3359, an abrasion resistance of 26.6% after 100 Taber cycles with CS-10 F wheels and a 1000 gram load according to ASTM test D1044.

Comparative Example 4

Five parts per hundred of 1-hydroxycyclohexylphenyl ketone (IRGACURE 184 brand photoinitiator from Ciba) is mixed with Sartomer SR 9003 brand monomer (propox neopentyl glycol diacrylate) and coated on a glass test substrate and cured by exposure to UV radiation to produce a 10 micrometer thick coating (plus or minus 2 micrometers) having a universal hardness of 61.1 N/mm$^2$; a Vickers hardness of 4.9; a modulus of 1.62 GPa; a light transmittance of 91.6 percent; an initial haze of 0.06% according to ASTM test D1003/D1044; a pencil hardness of B according to ASTM test D3363; and a MEK rub test of 50 rubs according to ASTM test D5402 and a stain resistance score (for 35 micrometer coatings on a polycarbonate substrate) according to ASTM test D1308 of 2, 2, 0, 4, 1, 1, 0 and 4 respectively for tap water, ethanol, vinegar, black dye, dilute caustic soda, yellow mustard, Betadine and ammonia water.

When coated on a polycarbonate test substrate and cured by exposure to UV radiation to produce a 35 micrometer thick coating (plus or minus 2 micrometers), the coating has a universal hardness of 74.3 N/mm$^2$; an initial haze of 0.63% according to ASTM test D1003/D1044; a pencil hardness of 2B according to ASTM test D3363; a MEK rub test of greater than 200 rubs according to ASTM test D5402; an adhesion of 1B according to ASTM test D3359, an abrasion resistance of 47.1% after 100 Taber cycles with CS-10 F wheels and a 1000 gram load according to ASTM test D1044

Comparative Example 5

Five parts per hundred of 1-hydroxycyclohexylphenyl ketone (IRGACURE 184 brand photoinitiator from Ciba) is mixed with Sartomer CD 580 brand monomer (ethoxylated cyclohexane dimethanol diacrylate) and coated on a glass test substrate and cured by exposure to UV radiation to produce a 10 micrometer thick coating (plus or minus 2 micrometers) having a universal hardness of 36.4 N/mm²; a Vickers hardness of 2.98; a modulus of 0.92 GPa; a light transmittance of 91.1 percent; an initial haze of 0.04% according to ASTM test D1003/D1044; a pencil hardness of B according to ASTM test D3363; and a MEK rub test of greater than 100 rubs according to ASTM test D5402 and a stain resistance score (for 35 micrometer coatings on a polycarbonate substrate) according to ASTM test D1308 of 0, 1, 1, 4, 1, 2, 2 and 3 respectively for tap water, ethanol, vinegar, black dye, dilute caustic soda, yellow mustard, Betadine and ammonia water.

When coated on a polycarbonate test substrate and cured by exposure to UV radiation to produce a 35 micrometer thick coating (plus or minus 2 micrometers), the coating has a universal hardness of 49.1 N/mm²; an initial haze of 0.60% according to ASTM test D1003/D1044; a pencil hardness of 3B according to ASTM test D3363; a MEK rub test of greater than 200 rubs according to ASTM test D5402; an adhesion of 0B according to ASTM test D3359, an abrasion resistance of 32.5% after 100 Taber cycles with CS-10 F wheels and a 1000 gram load according to ASTM test D1044.

Comparative Example 6

Five parts per hundred of 1-hydroxycyclohexylphenyl ketone (IRGACURE 184 brand photoinitiator from Ciba) is mixed with Sartomer CD 581 brand monomer (ethoxylated cyclohexane dimethanol diacrylate) and coated on a glass test substrate and cured by exposure to UV radiation to produce a 10 micrometer thick coating (plus or minus 2 micrometers) having a universal hardness of 18.9 N/mm²; a Vickers hardness of 2.81; a modulus of 0.39 GPa; a light transmittance of 91.3 percent; an initial haze of 0.02% according to ASTM test D1003/D1044; a pencil hardness of less than B according to ASTM test D3363; anal a MEK rub test of 30 rubs according to ASTM test D5402 and a stain resistance score (for 35 micrometer coatings on a polycarbonate substrate) according to ASTM test D1308 of 2, 1, 0, 5, 2, 2, 5 and 2 respectively for tap water, ethanol, vinegar, black dye, dilute caustic soda, yellow mustard, Betadine and ammonia water.

When coated on a polycarbonate test substrate and cured by exposure to UV radiation to produce a 35 micrometer thick coating (plus or minus 2 micrometers), the coating has a universal hardness of 9.32 N/mm²; an initial haze of 0.63% according to ASTM test D1003/D1044; a pencil hardness of 3B according to ASTM test D3363; a MEK rub test of greater than 200 rubs according to ASTM test D5402; an adhesion of 0B according to ASTM test D3359, an abrasion resistance of 36.8% after 100 Taber cycles with CS-10 F wheels; and a 1000 gram load according to ASTM test D1044.

Comparative Example 7

Five parts per hundred of 1-hydroxycyclohexylphenyl ketone (IRGACURE 184 brand photoinitiator from Ciba) is mixed with Sartomer CD 582 brand monomer (propoxylated (cyclohexane dimethanol diacrylate) and coated on a glass test substrate and cured by exposure to UV radiation to produce a 10 micrometer thick coating (plus or minus 2 micrometers) having a universal hardness of 16.9 N/mm²; a Vickers hardness of 1.81; a modulus of 0.38 GPa; a light transmittance of 91.5 percent; an initial haze of 0.08% according to ASTM test D1003/D1044; a pencil hardness of H according to ASTM test D3363; and a MEK rub test of 30 rubs according to ASTM test D5402 and a stain resistance score (for 35 micrometer coatings on a polycarbonate substrate) according to ASTM test D1308 of 1, 2, 2, 5, 1, 2, 1 and 3 respectively for tap water, ethanol, vinegar, black dye, dilute caustic soda, yellow mustard, Betadine and ammonia water.

When coated on a polycarbonate test substrate and cured by exposure to UV radiation to produce a 35 micrometer thick coating (plus or minus 2 micrometers), the coating has a universal hardness of 6.80 N/mm²; an initial haze of 0.60% according to ASTM test D1003/D1044; a pencil hardness of 3B according to ASTM test D3363; a MEK rub test of greater than 200 rubs according to ASTM test D5402; an adhesion of 0B according to ASTM test D3359, an abrasion resistance of 50.8% after 100 Taber cycles with CS-10 F wheels and a 1000 gram load according to ASTM test D1044.

CONCLUSION

In conclusion, while the instant invention has been described above according to its preferred embodiment, it can be modified within the spirit and scope of this disclosure. This application is therefore intended to cover any variations, uses, or adaptations of the instant invention using the general principles disclosed herein. Thus, the instant application is intended to cover such departures from the present disclosure as come within the known or customary practice in the art to which this invention pertains and which fall within the limits of the following claims.

What is claimed is:

1. A mixture of compounds useful to make a polymer or a prepolymer, the mixture of compounds comprising compounds having the formula I:

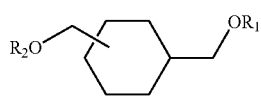

I wherein $R_1$ is H, acryloyl, methacryloyl or vinyl, wherein $R_2$ is acryloyl, methacryloyl or vinyl, wherein compounds having the formula I consist of a mixture of cis and trans-1,3- and 1,4-substituted cyclohexane and wherein the trans 1,4-substituted cyclohexane content of the compounds having the formula I is less than forty mole percent.

2. The mixture of compounds of claim 1, wherein the trans-1,4-substituted cyclohexane content of the compounds having the formula I is less than twenty five mole percent.

3. The mixture of compounds of claim 1, wherein the trans-1,4-substituted cyclohexane content of the compounds having the formula I is less than fifteen mole percent.

4. The mixture of compounds of any of claims 1-3, wherein the mixture of compounds is a liquid at room temperature.

5. The mixture of compounds of any of claims 1-3 useful to make a scratch resistant coating, further comprising colloidal inorganic nanoparticles or inorganic fillers.

6. A process for producing a mixture of compounds comprising compounds having the formula II:

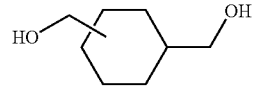

II wherein compounds having the formula II consist of a mixture of cis and trans-1,3-and 1,4-methanol substituted cyclohexane and wherein the trans-1,4-methanol substituted cyclohexane content of the compounds having the formula II is less than twenty five mole percent, characterized by the step of: distilling a mixture of cis and trans-1,3- and 1,4- methanol substituted cyclohexane wherein the trans-1,4-methanol substituted cyclohexane content of the compounds is greater than twenty five mole percent to produce a distilled fraction and a residue fraction, the residue fraction being the mixture of cis and trans-1,3- and 1,4-methanol substituted cyclohexane wherein the trans-1,4-methanol substituted cyclohexane content of the compounds having the formula II is less than twenty five mole percent.

7. The process of claim 6, wherein the trans-1,4-methanol substituted cyclohexane content of the compounds having the formula II is less than fifteen mole percent.

8. A prepolymer comprising units having the formula III:

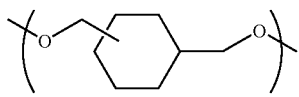

III wherein the units having the formula III consist of a mixture of cis and trans-1,3- and 1,4- substituted cyclohexane and wherein the trans-1,4-substituted cyclohexane content of the units having the formula III is less than forty mole percent and wherein the prepolymer is selected from the group consisting of polyester acrylates, polyester methacrylates, polycarbonate acrylates, polycarbonate methacrylates, polyurethane acrylates and polyurethane methacrylates.

9. The prepolymer of claim 8, wherein the trans-1,4-methanol substituted cyclohexane content of the compounds having the formula III is less than twenty five mole percent.

10. The prepolymer of claim 8, wherein the trans-1,4-methanol substituted cyclohexane content of the compounds having the formula III is less than fifteen mole percent.

* * * * *